US00PP10030P

Jnited States Patent [19]

ridgen et al.

[11] Patent Number: Plant 10,030

[45] Date of Patent: Sep. 16, 1997

4] ALSTROEMERIA PLANT NAMED 'SWEET LAURA'

5] Inventors: Mark P. Bridgen, Storrs, Conn.; Chunsheng Lu, Watsonville, Calif.; Michael Neuroth, Lumni, Wash.

3] Assignees: The University of Connecticut, Storrs, Conn.; Coast Alpine Nursery, Lummi, Wash.

1] Appl. No.: 573,201

2] Filed: Dec. 15, 1995

1] Int. Cl.[6] ..... A01H 5/00

2] U.S. Cl. ..... Plt./87.1

3] Field of Search ..... Plt./87.1

5] References Cited

PUBLICATIONS iley, C.H. and Bailey, E.Z., *Hortus Third*, p. 62, Mac-llan Publishing, N.Y. (1976).

*imary Examiner*—Howard J. Locker

*Attorney, Agent, or Firm*—Hamilton, Brook, Smith & Reynolds, P.C.

[57] ABSTRACT

This new and distinct cultivar of Alstroemeria named 'Sweet Laura' is characterized by its unique features of sweet fragrance, yellow flower color, vigorous growth, cold tolerance, and strong, upright floral stems. It is the first commercial Alstroemeria plant with fragrant flowers. The three outer tepals of the flowers are yellow with an orangish-red color at the tips that often emanates throughout the length of the tepals; the extreme tips of these tepals are green. The three inner tepals are also yellow, but their orangish-red region is absent or restricted to the extreme tip. The inner tepals also have narrow, longitudinal light brown streaks that radiate from the base to the tip. The streaking occurs with less frequency on the lower tepal. The plant is also distinguished by its long (80 to 85 cm), strong flowering stems with narrow long-lasting dark green leaves and its upright and vigorous growth habit. There is a continuous production of flowers on its umbel arrangement of inflorescences throughout its blooming season.

1 Drawing Sheet

SUMMARY OF THE INVENTION

This new and distinct cultivar of the botanical genus stroemeria (Lily-of-the-Incas, Peruvian Lily, or Inca Lily) a product of our Alstroemeria breeding program at the iversity of Connecticut in Storrs, Conn. The primary jective of this breeding program was the creation of new stroemeria cultivars for cut flowers, pot production and rden cultivation. This Alstroemeria plant originated from ibryo culture, designated as 0C1204, resulting from sses of species selected from breeding stock at the iversity of Connecticut and Coast Alpine Nursery, mmi Island, Wash.

This plant was selected for propagation because of its tinctive flower fragrance, yellow flower color, continuous wering and strong, upright flower stems. Asexual propa-tion of this new plant by rhizome division was carried on der our direction at the University of Connecticut; suc-ssive generations of this plant have demonstrated that the tinctive characteristics of the plant hold true from gen-tion to generation and appear to be firmly fixed. Micro-pagation and traditional asexual propagation by rhizome ision of this new cultivar is now being carried on at the iversity of Connecticut.

This cultivar has been observed in the greenhouse and in field for several years but has not been observed under possible environmental conditions. The phenotype may y with variations in environment such as light intensity, nperature, nutrition and daylength.

BRIEF DESCRIPTION OF THE DRAWING

This new cultivar of Alstroemeria plant is illustrated by accompanying photographic drawing in full color show-; three blooms from an umbel of the plant. The color nditions are believed to be as close to the specified colors is possible to obtain by conventional photographic pro-dures.

DETAILED DESCRIPTION OF THE NEW VARIETY

The following is a detailed description of our new Alstroemeria plant with color designations according to the R.H.S. Colour Chart of The Royal Horticultural Society of London, England. The following observation, measurements, and comparisons describe plants grown in Storrs, Conn. under greenhouse conditions and field conditions in full sun.

The Plant

Origin: Seedling derived from ovule cultured hybrid embryos.

Parentage:

*Seed parent.*—*Alstroemeria aurea.*

*Pollen parent.*—*Alstroemeria caryophyllaea.*

Classification:

*Botanic.*—Alstroemeria hybrid L.

*Commercial.*—Alstroemeria; Lily-of-the-Incas; Inca Lily; Peruvian Lily.

Form: Herbaceous plant arising from an underground rhizome and having long, strong, and upright growing floral stems with flower-bearing cymes of umbel-like form at its top.

Height: Approximately 80 to 85 cm.

Growth: Strong and upright.

Root stock: Tuberous.

Foliage:

*Quantity.*—Many.

*Number of leaves.*—Average of 27 leaves per vegetative stem. Average of 15 leaves per floral stem.

*Size of leaf.*—Vegetative stem: 10 cm (length)×2.2 cm (diameter at the widest point). Floral stem: 10 cm (length)×1.8 cm (diameter at the widest point).

*Leaf shape.*—Simple, linear, resupinate leaves with parallel venation that are arranged alternatively; the shape of the leaves is elongated elliptic with extended bases and broadly acuminate apices; leaf margins are entire.

*Texture.*—Glabrous leaf surface.
*Color.*—Dark green (137 A) on both upper and under sides.
Vegetative stem length: 70 to 75 cm.
Rhizomes:
*Color.*—White.

The Bud

Form: Pear shaped becoming long and more pointed just before opening.
Size:
*Diameter.*—Approximately 0.9 to 1 cm before opening.
*Length.*—Approximately 2.5 to 2.8 cm before opening.
Calyx: This plant's flower bud has no separate calyx and corolla; the six tepals of the flower are a perianth and divide simultaneously.
Opening rate: Normal.
Peduncle:
*Length.*—3.7 to 4.2 cm. (primary floret).
*Color.*—Green turning dark green/yellow as it reaches anthesis.

The Flower

Blooming habit: Continuous and profuse after flower initiation.
Flower size: Medium.
*Diameter.*—Approximately 4.0–4.5 cm.
Depth.—*Approximately* 4.0–4.5 cm.
Number of florets/inflorescence: Average 7.
Borne: Singly.
Shape: Flowers are zygomorphic, protandrous, and epigynous with inferior ovaries; flowers arise in a terminal bracted umbel of cymes. Mature blooms are funnel-shaped with repel tips curling slightly outward.
Petalage:
*Number of petals.*—Six tepals.
*Arrangement.*—Two concentric circles of three tepals each.
*Form.*—The three outer tepals are spatulate with emarginate to mucronate apices that pinch together. The extreme outer 1–2 mm tip is greenish. The three inner tepals are oblanceolate-spatulate but are more narrow than the 3 outer tepals and have apiculate apices.
*Texture.*—Leathery.
*Appearance.*—Shiny.
*Color of petals.*—Outer Tepals: Yellow Color 12 A-B. Distal portions of each apex is orange-red 31 A with various degrees of gradation of this color emanating down the central parts of the two lower tepals, and to some extent, the upper tepal. The spread of the orange-red color becomes most intense under high light intensities. In most cases there are no spots or streaks in the outer tepals. When florets first open, there is a slight green color (151 A) down the center of the tepals that changes to yellow or remains to a slight extent on the perimeter of the orange-red region. The extreme apex is light green (137 D). Inner Tepals: Yellow 12 A-B becoming most intense as the flower ages. There are numerous light brown/red (53A/59 A) narrow, longitudinal streaks radiating throughout from base to tip. The streaks are less frequent on the lower tepal. The orangish-red (31 A) region is absent or restricted to the extreme apex.
Peduncle:
*Length.*—3.7 to 4.2 cm.
*Color.*—Green.
Persistence: Tepals fall off at senescence.
Fragrance: Sweet.
Lasting quality:
*On plant.*—15 to 22 days.
*As a cut flower.*—8 to 12 days in water.
Main stem or stalk:
*Length.*—80 to 85 cm.
*Character.*—Strong and upright.
Number of leaves: Average of 15 leaves per floral stem.
Size of leaves on floral stem:
*Length.*—10–12 cm.
*Width.*—1.5–1.8 cm at widest point.

Reproductive Organs

Stamens:
*Number.*—Six.
*Arrangement.*—One opposite each tepal.
Anthers:
*Size.*—7 mm (length)×2 mm (width).
*Color.*—Orange-red (3IA).
Filaments:
*Length.*—Approximately 4 cm.
*Color.*—Orange-red.
Pistils:
*Number.*—One.
*Length.*—4 to 4.3 cm.
*Color.*—Yellow stigma, orange-red style.
Stigma:
*Color.*—Yellow.

The Fruit

Fertility: Sterile diploid (2n=2x=16).
Shape: Capsular.
Color at Maturity: Dark green.

This plant of Alstroemeria is characterized by its unique features of sweet fragrance, yellow flower color, vigorous growth, cold tolerance, and strong, upright floral stems. This plant is known to be hardy in USDA Zone 5 and has been grown in Zone 4. To the best of our knowledge, this is the first commercial Alstroemeria plant with fragrant flowers and does not closely resemble that of any other previously known to us. The three outer tepals of the flowers are yellow with an orangish-red color at the tips that often emanates throughout the length of the tepals; the extreme tips of these tepals are green. The three inner tepals are also yellow, but their orangish-red region is absent or restricted to the extreme tip. The inner tepals also have narrow, longitudinal light brown streaks that radiate from the base to the tip. The streaking occurs with less frequency on the lower tepal. The plant is also distinguished by its long (80 to 85 cm), strong flowering stems with narrow long-lasting dark green leaves and its upright and vigorous growth habit. There is a continuous production of flowers on its umbel arrangement of inflorescences throughout its blooming season. This plant will flower continuously in a greenhouse environment if given cool rhizome temperatures (50°–65° F.), long photoperiods and high light intensities. When grown outside in USDA Zone 5, 'Sweet Laura' plants will begin to flower in June and will flower continuously until the plants freeze.

We claim:

1. A new and distinctive Alstroemeria plant substantially as shown herein and described, distinguished by its sweet fragrance, unique flower color, strong and upright growth habit, long floral stems, narrow dark green leaves and continuous flowering habit.

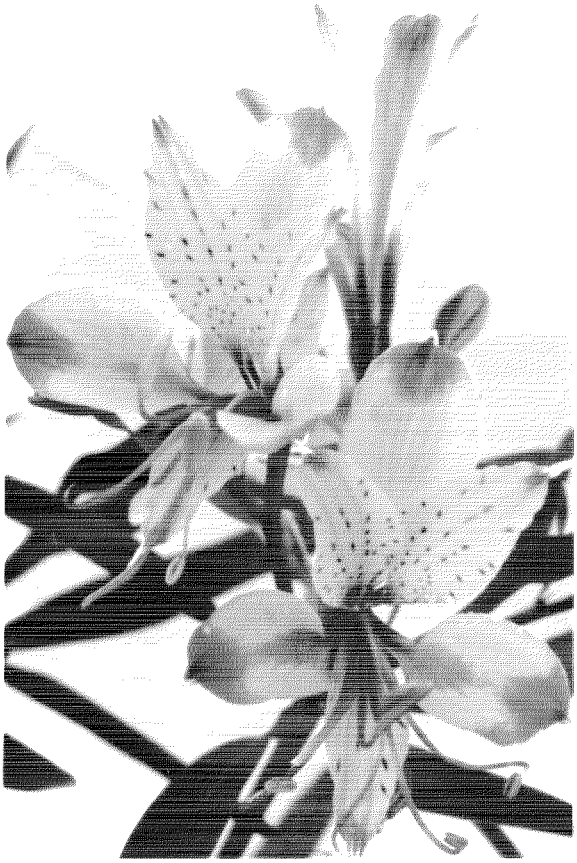

* * * * *